United States Patent [19]

Brevetti

[11] Patent Number: 4,968,719

[45] Date of Patent: Nov. 6, 1990

[54] METHOD FOR TREATING VASCULAR DISEASE

[75] Inventor: Gregorio Brevetti, Naples, Italy

[73] Assignee: Sigma Tau, Industrie Farmaceutiche Riunite SpA, Rome, Italy

[21] Appl. No.: 331,737

[22] Filed: Apr. 3, 1989

[51] Int. Cl.$^5$ ............................................ A61K 31/205
[52] U.S. Cl. .................................... 514/556; 514/824
[58] Field of Search ................................. 514/556, 824

[56] References Cited

U.S. PATENT DOCUMENTS 4,474,812  10/1984  Cavazza ............................. 514/556

OTHER PUBLICATIONS

G. Brevetti et al., *Circulation*, vol. 77, pp. 767–773 (1988).

*Primary Examiner*—Allen J. Robinson
*Attorney, Agent, or Firm*—Oblon, Spivak, McClelland, Maier & Neustadt

[57] ABSTRACT

L-carnitine is effective for the treatment of peripheral vascular diseases, such as intermittent claudication. Administration of L-carnitine to patients suffering from intermittent claudication results in a significant increase in the distance the patients can walk before experiencing claudication.

9 Claims, 2 Drawing Sheets

METHOD FOR TREATING VASCULAR DISEASE

BACKGROUND OF THE INVENTION

1. Field of the Invention:

The present invention relates to a method for treating peripheral vascular diseases.

2. Discussion of the Background:

The most important problem in the treatment of obstructive vascular disease is to make the energy supply adequate to the metabolic demand in the hypoxic area. In peripheral vascular disease, this goal has been sought only by interventions aimed at increasing the blood flow to the ischemic muscle.

Vasodilators are the most often used drugs in the therapy of chronic obstructive vascular disease, although their efficacy is far from being proved (see J. D. Coffmann, et al., *Ann. Intern. Med.*, 76, 35 (1972); and V. Hansteen, et al., *Acta Med. Scand.* [*Suppl.*], 556, 3 (1974)). Much more effective seem to be drugs capable of reducing blood viscosity. Among these, pentoxifylline has been demonstrated to increase walking distance (see G. Brevetti, et al., *Il Progresso Medico*, 35, 363 (1979); and J. M. Porter, et al., *Am. Heart J.*, 104, 66 (1982)) as a result of increased blood flow and enhanced tissue oxygenation in the affected limb (see G. Brevetti, et al., in *Adaptability of Vascular Wall*, Z. Reims, et al., eds., Springer-Verlag, Berlin, 1980, p. 555; and A. M. Ehrly, *J. Med.*, 10, 331 (1979)). Other reports, however, failed to demonstrate any objective benefit (see A. Mashiah, et al., *Br. J. Surg.*, 65, 342 (1978)).

Thus, there remains a need for a method to treat obstructive peripheral vascular diseases, such intermittent claudication.

SUMMARY OF THE INVENTION

Accordingly, one object of the present invention is to provide a novel method for the treatment of obstructive vascular diseases.

It is another object of the present invention to provide a novel method for the treatment of obstructive peripheral arterial diseases.

It is another object of the present invention to provide a novel method for the treatment of intermittent claudication.

These and other objects which will become apparent during the course of the following detailed description have been achieved by the inventor's discovery that the administration of a therapeutically effective amount of L-carnitine or a pharmaceutically acceptable salt thereof is an effective treatment of obstructive periferal vascular diseases, such as intermittent claudication.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1A:
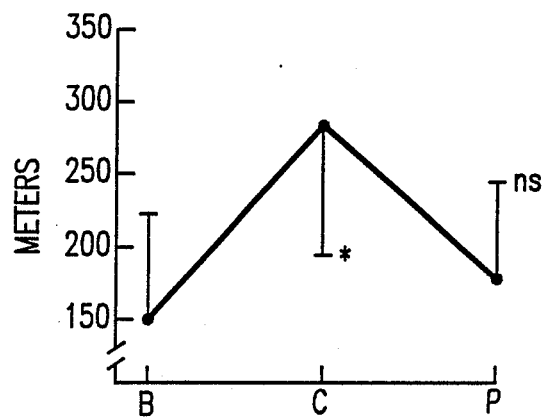
FIGS. 1a and 1b illustrate the effect of placebo and L-carnitine treatments on absolute claudication distance. Data are expressed as mean+SD. *: Different from baseline value, $p<0.01$; B=baseline value (after washout period); C=end of L-carnitine period; P=end of the placebo period.

L-Carnitine is a readily available compound, which is isolable, for example, from meat (see, e.g., Carter, et al., *Arch. Biochem. Biophys.*, 38, 405 (1952); and Colowick et al., *Methods in Enzymology*, Vol. III, Academic Press, New York, 1957, p. 660). In addition, the synthesis of L-carnitine has been reported by Tomita et al., *Z. Physiol. Chem.*, 169, 263 (1927) and Strack et al., *Z. Physiol. Chem.*, 318, 129 (1960). Either isolated naturally occurring or synthetic L-carnitine is suitable for the present method.

The present method may involve administering the L-carnitine as either the neutral inner salt (Zwitter ion form) or as a pharmaceutically acceptable salt. Suitable pharmaceutically acceptable salts include the acid addition salts and may contain as the anion: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, lactate, maleate, methanesulfonate, 2-naphthalanesulfonate, nicotinate, oxalate, palmitate, pectinate, persulfate, 3-phenylpropionate, picrate, pivalate, propionate, succinate, tartrate, thiocyanate, tosylate, and undecanoate. Of these salts, simple inorganic salts, such as salts of hydrogen halides are preferred. The hydrochloride is the particularly preferred salt.

The present method may be carried out by administering the L-carnitine in any suitable fashion, for example, parenterally, intravenously, or orally. Intravenous and oral administration are preferred.

While dosage will vary with the specific severity of the disease condition to be alleviated, in the case of oral administration, a suitable dose is in the range of 0.1 to 10 g b.i.d. (bis in die, twice daily). A preferred oral dosage is from 1 to 5 g b.i.d., and a particularly preferred oral dosage is about 2 g b.i.d. In the case of intravenous administration, the L-carnitine may be administered in the form of a bolus followed by infusion. The bolus is suitably from 0.1 to 10 g, preferably from 1 to 5 g, most preferably about 3 g. The infusion is suitably from 0.1 to 10 mg/kg of body weight/min., preferably from 1 to 5 mg/kg of body weight/min., most preferably about 2 mg/kg of body weight/min. The infusion is suitably carried out for a time of from 1 min. to 2 hrs., preferably from 10 min. to 1 hr., most preferably about 30 min. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

The present method may be carried out by administering the L-carnitine as a pharmaceutical composition containing any suitable carrier or excipient. The L-carnitine may be administered in any suitable form, such as, for example, a pill, a tablet, a troche, a capsule, a powder, a chewing gum, a wafer, an elixer, a suspension, a syrup or a solution.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, coatings. Thus, tablets or pills may be coated with sugar, shellac, or other enteric coating agents. A syrup may contain, in addition to the active compound, sucrose as a sweetening agent and certain preservatives, dyes and colorings and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The preparation can be enclosed in ampoules, disposable syringes or multiple dose vials made of glass or plastic.

The present method may be used to treat obstructive peripheral vascular diseases. In particular, the present method may be used to treat obstructive arterial disorders such as arterial occlusion, arterial spasm, arteriosclerosis obliterans, thromboangiitis obliterans (Buerger's disease), and atherosclerosis. The present method is particularly effective for the treatment of intermittent claudication, which may be defined as a pain in the calf muscles occurring during walking but which subsides with rest. The application of the present method to the treatment of intermittent claudication is discussed further below by presenting exemplary embodiments which are given for illustration of the invention and are not intended to be limiting thereof.

EXAMPLES

The effects of L-carnitine and placebo treatments of patients suffering from intermittent claudication were assessed in regard to hemodynamic effects, clinical effects, metabolic effects, and muscle carnitine content.

Patients and Methods

A total of 56 patients referred to an outpatient clinic for intermittent claudication were enrolled in the study. They gave informed consent before participation. All of them had been affected by peripheral arterial insufficiency at the second stage of Fontaine's classification (i.e., claudication on effort without pain at rest and/or trophic lesions in the affected leg) for at least 1 year before enrollment in the study. The diagnosis was established in advance on the basis of history, physical examination, impedance plethysmography, and decrease in the ankle/arm systolic blood pressure ratio after exercise. Patients with heart failure, coronary artery disease, and severe hypertension were excluded from the study. At the time of the first visit, all of the patients were treated with one or more of the following drugs: flunarizine, papaverine, pentoxifylline, and raubasine. A pretrial drug washout period of 2 weeks was allowed in all cases. During the entire period of the study, diuretics and oral hypoglycemic agents were the only drugs allowed. All tests were carried out in the morning after an overnight fast in a quiet room at the constant temperature of $21 + \pm 1°$ C. All patients were on a low-fat, low-cholesterol diet; diabetics were also on a standard low-carbohydrate diet (150 g/24 hr). Ankle/brachial systolic blood pressure ratio was obtained by Doppler ultrasound. The blood perfusion was measured by impedance plethysmography according to the method of Nyober et al. (*Am. Heart J.*, 87, 704 (1974)) and was calculated from an average of five consecutive waves. Walking distance before the occurrence of claudication was measured by treadmill and expressed as absolute walking distance (AWD), i.e., the maximum distance in meters walked by the patient a a speed of 2.5 mph and a grade of 7 degrees.

Hemodynamic assessment

After drug washout, 18 patients (17 men, one woman) ranging in age from 51 to 66 years (mean $60.3 \pm 4.1$) were randomly assigned to receive placebo or L-carnitine (3 g iv as a bolus, followed by continuous infusion of 2 mg/kg/min for 30 min). Heart rate, arterial blood pressure, ankle/brachial systolic blood pressure ratio of the affected limb, and blood flow were evaluated under control conditions and 2, 4, 6, 8, 10, 15, 20, and 30 min. after the bolus. A week later, patients crossed over to the other treatment and the same protocol was followed.

Intravenous administration of carnitine did not modify the blood perfusion in the affected limb. Blood flow and ankle/brachial systolic blood pressure ratio remained unchanged at all times of recording compared with baseline values. Similarly, no statistical difference in these variables was found between placebo and carnitine treatment (see Table 1).

TABLE 1

Effect of placebo (P) and intravenous L-carnitine (C) on perfusion volume and ankle/brachial systolic blood pressure ratio

| Assessment | Treatment | Baseline | Times of recording (min) | | | | | | | |
| --- | --- | --- | --- | --- | --- | --- | --- | --- | --- | --- |
| | | | 2 | 4 | 6 | 8 | 10 | 15 | 20 | 30 |
| Perfusion volume (ml/min/100 mg tissue) | P | 2.02 ± 0.95 | 2.10 ± 0.89 | 2.00 ± 0.99 | 2.05 ± 0.94 | 2.12 ± 0.92 | 2.12 ± 0.96 | 2.07 ± 0.98 | 2.04 ± 0.98 | 2.03 ± 0.98 |
| | C | 2.06 ± 0.87 | 2.11 ± 0.88 | 2.15 ± 1.02 | 2.05 ± 0.93 | 2.02 ± 0.87 | 2.17 ± 0.97 | 2.19 ± 0.90 | 2.14 ± 1.01 | 2.08 ± 0.83 |
| Ankle/brachial systolic | P | 0.62 ± | 0.62 ± | 0.63 ± | 0.61 ± | 0.62 ± | 0.62 ± | 0.62 ± | 0.62 ± | 0.63 ± |

TABLE 1-continued

Effect of placebo (P) and intravenous L-carnitine (C) on perfusion volume and ankle/brachial systolic blood pressure ratio

| Assessment | Treatment | Baseline | Times of recording (min) | | | | | | | |
|---|---|---|---|---|---|---|---|---|---|---|
| | | | 2 | 4 | 6 | 8 | 10 | 15 | 20 | 30 |
| blood pressure ratio | | 0.15 | 0.15 | 0.16 | 0.14 | 0.16 | 0.16 | 0.16 | 0.15 | 0.15 |
| | C | 0.65 ± 0.14 | 0.65± 0.15 | 0.66 ± 0.15 | 0.67 ± 0.15 | 0.66 ± 0.15 | 0.66 ± 0.16 | 0.67 ± 0.14 | 0.69 ± 0.15 | 0.67 ± 0.15 |

Data expressed as mean ± SD.

B. Clinical assessment

Two double-blind, cross-over studies were carried out to assess the ability of L-carnitine to improve walking distance when given orally for a long-term or intravenously for a short-term treatment. To ensure that the patient admitted to the double-blind treatment phase of the study had a stable AWD, three treadmill tests were conducted on all patients during the second week of the washout period, and only those exhibiting a change in AWD of 20% or more were included in this protocol.

The effect of the oral treatment was assessed in 20 male patients aged 40 to 69 years (mean 59.8±7.0) who fulfilled all the inclusion criteria. Patients entered the first drug treatment phase, in which they were randomly assigned to receive placebo or L-carnitine (2 g b.i.d., orally). Placebo and carnitine tablets were identical in size, shape, and color. After 3 weeks, each patient crossed over to the other drug, and treatment was continued for an additional 3 weeks. At the end of each treatment period, at 9 A.M., before the morning dose, blood flow and ankle/brachial systolic blood pressure ratio were measured in the affected limb at rest. Patients then performed a treadmill test, during which arterial blood pressure and the electrocardiogram were monitored continuously and AWD was assessed. The evaluation of subjective symptoms such as coldness, paresthesias, tiredness, and pain during walking was another aim of this study. The intensity of each symptom was scored on a six-point scale: $-3$=total relief, $-2$=marked improvement, $-1$=slight improvement 0=no change, 1=slight deterioration, 2=marked deterioration.

The effect of short-term intravenous administration of L-carnitine was assessed in an additional eight patients who were randomly assigned to placebo or L-carnitine (3 g iv as a bolus followed by continuous infusion of 2 mg/kg/min for 30 min.). After 1 week patients received the other treatment. At the end of the infusion, blood flow and ankle/arm systolic blood pressure ratio were measured at rest. Patients then performed treadmill exercise and AWD was assessed.

Figure 1B:
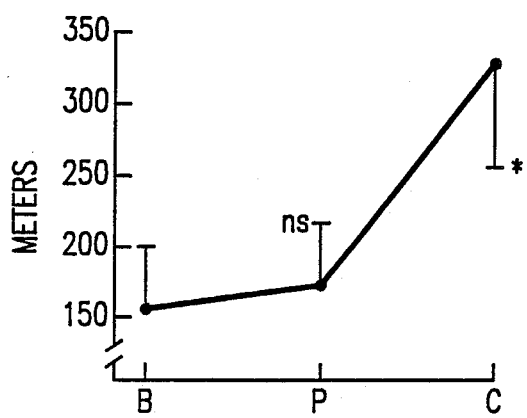

The analysis of variance, which did not show an interaction between treatments and periods, demonstrated that carnitine was able to induce a marked increase in AWD as compared with placebo. In the long-term study, AWD was 174.7±63.1 m with placebo and 306.5±121.8 m ($p<0.01$) with carnitine. After the first phase of treatment, patients assigned to carnitine showed an increase in AWD from the drug washout value of 147.0±67 to 288.0±97 m ($p<0.01$); when the subjects crossed to placebo, AWD returned to a value similar to that observed after washout (178.0 ±66 m). In patients assigned to placebo, AWD was 155.0±64 m after washout and 171.0±63 m (NS) after the first phase of treatment; when they crossed to carnitine, AWD increased to 324.0±146 m ($p<0.01$). These data are shown in FIG. 1.

This improvement was independent from the severity of arterial disease, since percent changes in walking distance did not correlate with AWD nor with the ankle/arm systolic blood pressure ratio. No statistical difference between placebo and carnitine was found in the resting values of blood flow and ankle/arm systolic blood pressure ratio. Changes in heart rate and blood pressure induced by exercise during treatment with placebo were not modified by carnitine.

Table 2 illustrates the changes in subjective symptoms. Patients assigned to placebo showed slight changes after the first phase of treatment; when they crossed to carnitine, all symptoms improved. Patients assigned to carnitine reported improvements in all symptoms compared with the washout period after the first phase of treatment; this improvement vanished when they crossed to placebo. As shown in Table 2, many of the patients reported marked improvement or total relief of symptoms during treatment with L-carnitine. As a consequence, comparison between treatments by the Mann-Whitney U test indicated a significant improvement ($p<0.01$) after L-carnitine.

With the exception of one patient who experienced pyrosis during both placebo and carnitine treatment, no side effects were observed during the trial.

In the short-term study, intravenous carnitine increased AWD from 171.0±32 m during placebo to 286.0 ±155 m ($p<0.5$). Therefore the intravenous administration of L-carnitine increased AWD by 67%, a value similar to that observed with oral treatment (75%).

Individual data on the ankle/arm systolic blood pressure ratio and the treadmill tests throughout the study are reported in Table 3.

TABLE 2

Changes in subjective symptoms observed throughout the study in patients randomly assigned to receive placebo (top) and in patients randomly assigned to receive carnitine (bottom)

| | Paresthesias | | Tiredness | | Pain during walking | | Coldness | |
|---|---|---|---|---|---|---|---|---|
| Patient | P vs WO | C vs P | P vs WO | C vs P | P vs WO | C vs P | P vs WO | C vs P |
| 1 | 0 | −3 | +1 | −3 | 0 | −2 | 0 | −2 |
| 2 | +1 | −3 | 0 | −3 | 0 | −3 | 0 | −2 |
| 3 | −1 | 0 | 0 | −1 | 0 | −1 | −1 | 0 |
| 4 | 0 | −1 | 0 | −2 | −1 | −2 | 0 | 0 |
| 5 | 0 | −1 | −1 | −1 | −1 | 0 | 0 | 0 |
| 6 | 0 | −2 | 0 | −3 | 0 | −2 | 0 | 0 |

TABLE 2-continued

Changes in subjective symptoms observed throughout the study in patients randomly assigned to receive placebo (top) and in patients randomly assigned to receive carnitine (bottom)

| | | | | | | | | |
|---|---|---|---|---|---|---|---|---|
| 7 | +1 | −2 | −1 | −3 | 0 | −3 | 0 | 0 |
| 8 | 0 | −2 | 0 | −2 | 0 | −1 | 0 | −1 |
| 9 | 0 | −3 | −1 | −2 | −1 | 0 | 0 | 0 |
| 10 | −1 | −3 | −1 | −3 | −1 | −3 | 0 | −1 |

| | C vs WO | P vs C | C vs WO | P vs C | C vs WO | P vs C | C vs WO | P vs C |
|---|---|---|---|---|---|---|---|---|
| 1 | −3 | +2 | −3 | +1 | −3 | −2 | −2 | 0 |
| 2 | −3 | +1 | −3 | +2 | −2 | +2 | −2 | −1 |
| 3 | −2 | +1 | −3 | +1 | −2 | 0 | −1 | 0 |
| 4 | −3 | +1 | −3 | +1 | −3 | +2 | −1 | 0 |
| 5 | −3 | 0 | −2 | +2 | −2 | +2 | 0 | 0 |
| 6 | −3 | +2 | −1 | +1 | −1 | −1 | 0 | 0 |
| 7 | −3 | +2 | −1 | +2 | −2 | +2 | −1 | 0 |
| 8 | −2 | +1 | −2 | +2 | −2 | +1 | 0 | 0 |
| 9 | 0 | 0 | 0 | 0 | −1 | 0 | 0 | 0 |
| 10 | −1 | +1 | −2 | +1 | −2 | +1 | −1 | +1 |

WO = washout; P = placebo; C = carnitine.
All symptoms were significantly ($p < .01$) improved by carnitine (Mann-Whitney U Test).

TABLE 3

Individual data of ankle/arm systolic blood pressure ratio and walking distance measured at the end of wash-out, placebo, and carnitine periods

| | Ankle/arm SBP ratio | | | Walking distance (m) | | |
|---|---|---|---|---|---|---|
| Patent | WO | P | C | WO | P | C |
| Long-term study | | | | | | |
| 1 | 0.71 | 0.65 | 0.61 | 118 | 122 | 302 |
| 2 | 0.59 | 0.73 | 0.85 | 302 | 290 | 578 |
| 3 | 0.53 | 0.46 | 0.57 | 196 | 198 | 254 |
| 4 | 0.53 | 0.60 | 0.58 | 143 | 156 | 327 |
| 5 | 0.56 | 0.46 | 0.45 | 181 | 227 | 232 |
| 6 | 0.60 | 0.58 | 0.51 | 90 | 88 | 241 |
| 7 | 0.56 | 0.57 | 0.71 | 107 | 103 | 303 |
| 8 | 0.73 | 0.71 | 0.69 | 130 | 133 | 209 |
| 9 | 0.90 | 0.66 | 0.70 | 143 | 194 | 205 |
| 10 | 0.90 | 0.94 | 0.95 | 200 | 202 | 604 |
| 11 | 0.78 | 0.70 | 0.61 | 176 | 207 | 388 |
| 12 | 0.85 | 0.80 | 0.85 | 94 | 78 | 251 |
| 13 | 0.62 | 0.58 | 0.70 | 104 | 148 | 146 |
| 14 | 0.60 | 0.56 | 0.56 | 83 | 98 | 279 |
| 15 | 0.50 | 0.46 | 0.50 | 142 | 203 | 163 |
| 16 | 0.85 | 0.77 | 0.73 | 139 | 174 | 362 |
| 17 | 0.62 | 0.52 | 0.66 | 191 | 254 | 338 |
| 18 | 0.30 | 0.29 | 0.37 | 152 | 150 | 203 |
| 19 | 0.69 | 0.58 | 0.60 | 295 | 300 | 428 |
| 20 | 0.66 | 0.61 | 0.63 | 180 | 168 | 318 |
| Mean | 0.65 | 0.61 | 0.64 | 158.2 | 174.7 | 306.5 |
| ± SD | 0.15 | 0.11 | 0.14 | 59.8 | 63.1 | 121.8 |
| Short-term study | | | | | | |
| 1 | 0.54 | 0.56 | 0.60 | 227 | 187 | 505 |
| 2 | 0.61 | 0.60 | 0.60 | 228 | 223 | 551 |
| 3 | 0.60 | 0.66 | 0.73 | 120 | 128 | 185 |
| 4 | 0.55 | 0.50 | 0.56 | 160 | 164 | 266 |
| 5 | 0.59 | 0.63 | 0.66 | 140 | 202 | 240 |
| 6 | 0.69 | 0.77 | 0.70 | 150 | 147 | 162 |
| 7 | 0.54 | 0.54 | 0.54 | 141 | 174 | 232 |
| 8 | 0.69 | 0.65 | 0.62 | 89 | 143 | 147 |
| Mean | 0.60 | 0.61 | 0.62 | 156.9 | 171.0 | 286.0 |
| ± SD | 0.06 | 0.08 | 0.06 | 49 | 32 | 155 |

SBP = systolic blood; other abbreviations as in Table 2.

C. Metabolic assessment

The metabolic changes induced by exercise were assessed, before and after carnitine administration, in six male patients (mean age 61.0±7.1 years). After inducement of local anesthesia with 1% procaine, catheters were placed into one radial artery and into the popliteal vein of the affected leg, i.e., as close as possible to the ischemic area. Control measurements were carried out on the following day. Ten milliliters of arterial and venous blood were drawn after 5 min. of standing. The patients then performed a treadmill exercise as described above, and blood samples were taken when the maximal walking distance was reached as well as 5 min. after cessation of exercise. Twenty-four hours later, carnitine was administered intravenously at the same dose as above. Blood samples were taken at rest, then exercise was started and blood samples drawn at the same walking distance as under control conditions and 5 min after exercise. By this method it was possible to assess the metabolic effect of L-carnitine on the ischemic muscle undergoing the same workload as with placebo. Plasma lactate and pyruvate concentrations were determined in duplicate by an enzymatic method (H. J. Hohorst, in *Methods of Enzymatic Analysis*, H. Bergmeyer, ed., Academic Press, New York, 1968, p. 266; and R. Czok, in *Methods of Enzymatic Analysis*, H. Bergmeyer, ed., Academic Press, New York, 1974, p. 1491).

Before carnitine treatment, the mean AWD was 168.0 ±34 m. After carnitin, none of the six patients experienced ischemic pain in the affected leg at the same walking distance. In the absence of carnitine, exercise induced an increase in popliteal venous lactate concentration from the rest value of 1.36±0.28 to 3.63±1.2 mmol/liter ($p<0.05$) After carnitine treatment, at the same walking distance as before, lactate concentration increased from 1.30±0.40 to 2.75±0.22 mmol/liter ($p<0.01$). In all patients, 5 min. after cessation of exercise, the popliteal venous lactate level was still higher than at rest, 2.83±0.6 mmol/liter ($p<0.01$) in the absence of carnitine, but only 1.96±0.55 mmol/liter ($p<0.01$) with carnitine. Actually, 5 min. after termination of the walking test, venous lacetate concentration increased by 107±16% as compared with the rest value in untreated patients; after treatment with carnitine the increase was only 54.2±32% ($p<0.01$).

Figure 2:
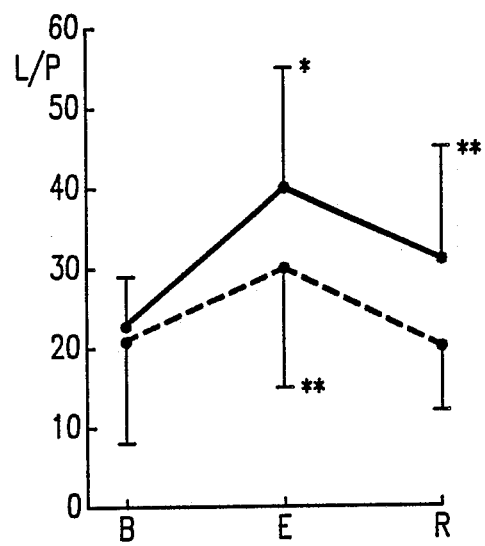
FIG. 2 illustrates the popliteal venous lactate/pyruvate (L/P) ratio at rest (B), during exercise (E), and during the recovery period (R), under control conditions (solid line) and after administration of L-carnitine (interrupted line). Data are expressed as mean+SD. *: Different from rest value, $p<0.05$; **: different from rest value, $p<0.01$.

Under basal conditions, popliteal venous pyruvate concentration rose during exercise from the rest value of 0.064±0.01 to 0.096±0.03 mmol/liter ($p<0.05$). Five minutes after the walking test it was 0.101±0.04 mmol/liter ($p<0.05$). Similar changes were observed after carnitine treatment (Table 4). Therefore, as shown in FIG. 2, in the absence of carnitine the popliteal venous lactate/pyruvate (L/P) ratio increased from 21.9±6 to 40.2±14 ($p<0.05$) during exercise, and 5 min. after exercise L/P was still higher than at rest (31.6±13; $p<0.01$) After carnitine treatment, the L/P ratio during exercise increased from 21.7±13 to 30.0±15 (p<0.01) and returned to the rest value during the recovery period (20.1±8). Throughout the study, L/P ratios were similar in the treated and in the control groups. Furthermore, arterial lactate and pyruvate concentration and L/P ratios were similar in treated and untreated patients at rest, during exercise, and after recovery (Table 4).

TABLE 4

Lactate and pyruvate concentrations (mmol/liter) at rest and during and after exercise (mean ± SD)

| | Venous | | | Arterial | | |
|---|---|---|---|---|---|---|
| | Rest | Exercise | Recovery | Rest | Exercise | Recovery |
| Lactate Control | 1.36 ± 0.28 | 3.63 ± 1.20 | 2.82 ± 0.60 | 0.97 ± 0.29 | 2.21 ± 0.70 | 1.50 ± 0.47 |
| p | | <.05 | <.01 | | <.01 | <.05 |
| Carnitine | 1.30 ± 0.41 | 2.75 ± 0.72 | 1.96 ± 0.55 | 0.83 ± 0.43 | 2.05 ± 1.12 | 1.45 ± 0.68 |
| p | | <.01 | <.01 | | <.01 | <.01 |
| Pyruvate Control | 0.064 ± 0.01 | 0.096 ± 0.03 | 0.101 ± 0.04 | 0.049 ± 0.01 | 0.148 ± 0.05 | 0.117 ± 0.04 |
| p | | <.05 | <.02 | | <.01 | <.01 |
| Carnitine | 0.072 ± 0.03 | 0.106 ± 0.04 | 0.108 ± 0.04 | 0.053 ± 0.02 | 0.093 ± 0.02 | 0.080 ± 0.02 |
| p | | <.01 | <.01 | | <.01 | <.05 | p values refer to differences from rest values.

D. Muscle carnitine assay

Carnitine and carnitine fractions were measured in the ischemic muscle of four patients before and after 15 days of oral L-carnitine supplementation (2 g bid). Muscle specimens, obtained from the gastrocnemius of the affected leg under local anesthesia, were frozen in liquid nitrogen-cooled isopentane and stored at −70° C. Free carnitine was assayed by the radiochemical method of Cederblad and Linstedt (*Clin. Chim. Acta*, 37, 235 (1972)) in the presence of 0.5 mM N-ethylmaleimide. Acid-soluble and insoluble acylcarnitines were measured upon alkaline hydrolysis, as described by Pearson and Tubbs (*Biochem. Biophys. Acta*, 84, 772 (1964)). Noncollagen proteins were determined according to the method of Lilienthal et al. (*J. Biol. Chem.*, 182, 501 (1950)).

Table 5 shows changes in total, free, and esterified carnitine concentrations induced by L-carnitine in patients with peripheral vascular disease. Normal values were obtained from six normal subjects matched to the patients with peripheral arterial disease with respect to age and sex, chosen from a group of 46 normal individual previously studied.

Before treatment, total carnitine in the biopsied muscle was 19.3±3.6 nmol/mg noncollagen protein, a value not different from that found in normal muscle. After treatment, total carnitine increased in all subjects to a level as high as 24.6±2.9 nmol/mg noncollagen protein (p<0.05), thus demonstrating a direct uptake of the administered L-carnitine by the biopsied muscle. The observed increase in total carnitine is accounted for by an increase in both free carnitine and short-chain acylcarnitine. In contrast, the concentration of long-chain acylcarnitine decreased, although not significantly, after L-carnitine supplementation. It must be noted that free and total carnitine values before treatment are within the normal range.

TABLE 5

Changes in free and esterified carnitine concentration induced by L-carnitine treatment in patients with peripheral arterial disease (mean SD, nmol/mg noncollagen protein)

| | PAD before treatment | PAD after treatment | Normals |
|---|---|---|---|
| Free carnitine | 16.31 ± 2.30 | 20.07 ± 4.67 | 16.46 ± 4.58 |
| Short-chain acylcarnitines | 2.49 ± 1.51 | 4.11 ± 2.54 | 3.40 ± 1.69 |
| Long-chain acylcarnitines | 0.51 ± 0.09 | 0.41 ± 0.27 | 0.88 ± 0.59 |
| Total carnitine | 19.31 ± 3.56 | 24.59 ± 2.94[A] | 21.15 ± 5.01 |

PAD = peripheral arterial disease.
[A]Significantly different from the pretreatment value: p < .05.

E. Statistical analysis

Comparison between placebo and carnitine treatment was performed by analysis of variance for a cross-over design. Differences from baseline were analyzed with the t test for paired data. The Mann-Whitney U test was used to compare the effect of the two treatments on clinical variables. Group values are expressed as mean±SD.

The results of the present double-blind, placebo-controlled study demonstrate that in patients with chronic obstructive vascular disease of the lower limbs, carnitine induces a statistically significant and clinically relevant increase in walking distance. Given the spontaneous fluctuation in the severity of intermittent claudication experienced by such patients, only an increase in AWD of 25% over baseline was accepted as clinically relevant. The results indicate that, compared with placebo, 12 of the 20 patients who completed the oral carnitine study showed an increase in AWD at 60% or more, four subjects had 25% to 59% improvement, and only four showed no difference in AWD between placebo and carnitine treatment. Moreover, the L/P ratio during recovery was still higher than at rest during treatment with placebo and returned to the rest value on carnitine.

A reasonable interpretation of these metabolic effects may be the following: Oxygen availability in skeletal muscle is critical for the conversion of pyruvate to either lactate or acetylcoenzyme A (acetyl-CoA). The latter reaction is catalyzed by pyruvate dehydrogenase, the activity of which is controlled by the acetyl-CoA/-CoA ratio (P. J. Randle, *Trends Biochem. Sci.*, 3, 217 (1978) and R. M. Denton, et al., *Essays Biochem.*, 15, 37 (1979)). Through the action of CoA:carnitine acetyl transferase, carnitine may decrease such a ratio (L. L. Bieber, et al., *Fed. Proc.*, 41, 2858 (1982)) and stimulate the activity of pyruvate-dehydrogenase, consequently preventing the formation of lactate. In patients with peripheral vascular disease, pyruvate oxidation is presumably limited by two conditions: (1) the inadequacy of oxygen supply and (2) the accumulation of acetyl-CoA caused by a decreased flux into the Krebs cycle.

Carnitine does not apparently influence tissue oxygen supply but is able to decrease the acetyl-CoA concentration by virtue of the presence of a very active CoA:-carnitine acetyl transferase in the muscular tissue (J. Bremer, *Physiol. Rev.*, 63, 1420 (1983) and I. Alkonyl, *FEBS Lett.*, 52, 265 (1975)). This assumption is supported by the finding that administration of carnitine resulted in a significant increase of total carnitine in muscles of the affected leg. Both the increase of free carnitine and short-chain acyl carnitine contributed to such an increase. These changes in the concentrations of muscular carnitine fractions indicate that part of the administered carnitine was taken up by muscles of the affected leg and that a consistent portion was transformed into short-chain acyl carnitine, presumably acetyl carnitine (J. Bremer, *Physiol. Rev.*, 63, 1420 (1983)). This implies that a corresponding amount of short-chain acyl-CoA, presumably acetyl-CoA, was removed along with a concurrent release of free CoA. The consequent decrease of the acetyl-CoA/CoA ratio would explain the above-mentioned stimulation of pyruvate dehydrogenase.

In the short-term exercise protocol, the preferentially utilized substrate was conceivably muscle glycogen or blood glucose (O. Bjorkman, in *Biochemical Aspects of Physical Exercise*, G. Benzi, et al., eds., Elsevier Sci. Pub., Amsterdam, 1986, pp. 245-260). As a consequence, a large increase of pyruvate production should be expected. The stimulation of pyruvate dehydrogenase activity by the increased availability of carnitine might explain both the decreased production of lactate and the higher yield of energy, resulting from pyruvate oxidation. It is well known that glucose utilization in anaerobic glycolysis yields 2 ATP, whereas glucose utilization in the aerobic pathway produces 36 ATP. This enhancement of pyruvate oxidation and, hence, in energy production may explain the improvement of walking ability after treatment with L-carnitine.

An additional mechanism by which treatment with carnitine might be beneficial is the removal of long-chain acyl-CoA (F. DiLisa, et al., *Biochem. Biophys. Res. Commun.*, 1341, 968 (1985)). An accumulation of these metabolites in oxygen-deficient conditions may be detrimental to the cellular membrane stability. An improvement of long-chain fatty acid utilization by supplemented L-carnitine seems to be ruled out by the observation that in muscles of the affected leg even before L-carnitine treatment, the concentration of total carnitine is above the value considered rate-limiting for the optimal fatty acid oxidation (C. S. Long, et al., *Neurology*, 32, 663 (1982)).

The results of this study show that carnitine allows ischemic skeletal muscle to reach a higher level of energy expenditure before claudication develops. Therefore L-carnitine represents an effective agent for treating peripheral vascular disease. Furthermore, because the mechanism of action of this factor differs from that of other available therapeutic agents, a combination of more traditional drugs with carnitine may be regarded as a useful means for treating this disease.

Thus, the present invention provides a new approach to the treatment of peripheral vascular disease. L-Carnitine, although not affecting general or regional hemodynamics, improves the walking ability of patients with intermittent claudication, probably through a metabolic mechanism.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the treatment of peripheral vascular disease, comprising administering to a patient in need thereof, a therapeutically effective amount of L-carnitine or a pharmaceutically acceptable salt thereof.

2. The method of claim 1, wherein said L-carnitine or pharmaceutically acceptable salt thereof is administered orally.

3. The method of claim 2, wherein said L-carnitine or pharmaceutically acceptable salt thereof is administered in an amount of from 1 to 5 g twice daily.

4. The method of claim 1, wherein said L-carnitine or pharmaceutically acceptable salt thereof is administered intraveneously.

5. The method of claim 1, wherein said disease is selected from the group consisting of arterial occlusion, arterial spasm, arteriosclerosis obliterans, thromboangiitis obliterans, and atherosclerosis.

6. A method for the treatment of intermittent claudication, comprising administering to a patient in need thereof a therapeutically effective amount of L-carnitine or a pharmaceutically acceptable salt thereof.

7. The method of claim 6, wherein said L-carnitine or pharmaceutically acceptable salt thereof is administered orally.

8. The method of claim 7, wherein said L-carnitine or pharmaceutically acceptable salt thereof is administered in an amount of from 1 to 5 g twice daily.

9. The method of claim 6, wherein said L-carnitine or pharmaceutically acceptable salt thereof is administered intraveneously.

* * * * *